United States Patent [19]

Steck et al.

[11] Patent Number: 4,575,458

[45] Date of Patent: Mar. 11, 1986

[54] MULTICOMPONENT ATTRACTANT FOR ARMYWORM MOTHS

[75] Inventors: Warren F. Steck; Edward W. Underhill; Melvin D. Chisholm; Berton K. Bailey, all of Saskatoon, Canada

[73] Assignee: Canadian Patents and Development Limited, Ottawa, Canada

[21] Appl. No.: 427,721

[22] Filed: Sep. 29, 1982

[51] Int. Cl.⁴ .................................... A01N 25/00
[52] U.S. Cl. ................................... 424/84
[58] Field of Search ................................ 424/84

[56] References Cited

PUBLICATIONS

Chem. Abstracts 94: 26114f Sato et al. 1981.
Chem. Abstracts 88: 131935y Gothlif et al. 1978.
Chem. Abstracts 93: 127094j 1980.
Chem. Abstracts 94: 115947x 1980.
Chem. Abstracts 95: 56284z 1981.
Chem. Abstracts 82: 122031z 1975.
Chem. Abstracts 67: 106302y 1967.
Chem. Abstracts 76: 82154j 1971.
Chem. Abstracts 77: 162128q 1972.
Chem. Abstracts 87: 149067f 1977.
Chem. Abstracts 95: 37039g 1981.

*Primary Examiner*—Albert T. Meyers
*Assistant Examiner*—John M. Kilcoyne
*Attorney, Agent, or Firm*—Alan A. Thomson

[57] ABSTRACT

Moths of the armyworm *Pseudaletia unipuncta* have been found to be attracted strongly to mixtures of three or four chemical compounds. The mixtures found to be the most powerful and specific attractants are those comprising:

(a) (Z)-11-hexadecenyl acetate
(b) (Z)-11-hexadecenol and
(c) (Z)-11-hexadecenal, preferably with
(d) (Z)-9-tetradecenyl acetate.

The respective weight ratios for the best effect were found to be approximately 10000:20:4:1.

11 Claims, 1 Drawing Figure

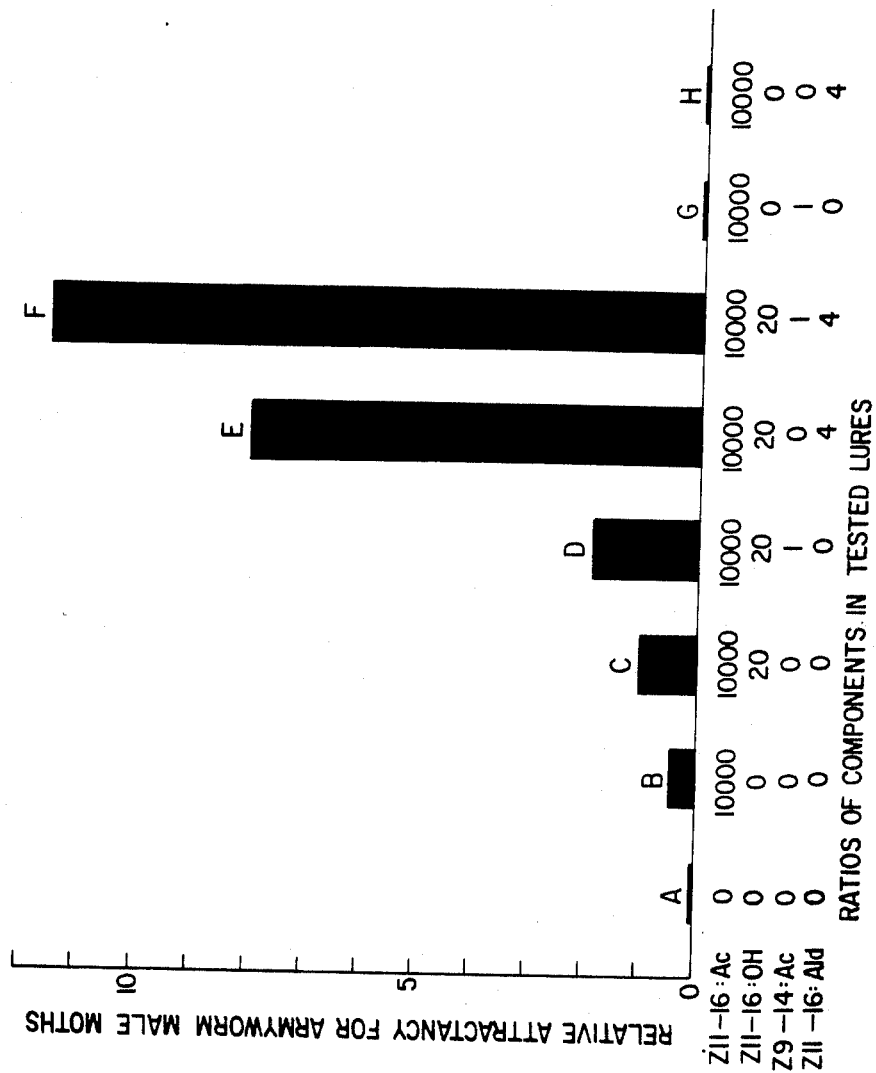

MULTICOMPONENT ATTRACTANT FOR ARMYWORM MOTHS

FIELD OF THE INVENTION

This invention is directed to a multicomponent artificial attractant for male moths of the armyworm *Pseudaletia unipuncta*. A unique and unexpected combination of chemicals has been found to constitute a powerful attractant highly specific for this species.

BACKGROUND OF THE INVENTION

*Pseudaletia unipunctra*, the true armyworm, is endemic on all continents, being an indiscriminate pest of field crops and horticultural species. The moth is known to be migratory and in Canada (and some other temperate regions) the species enters afresh each spring from the south. Because of this behaviour, the pest may appear suddenly in large numbers. The moths lay eggs in May/June which hatch into the damaging larval (armyworm) stage during June/July. There are two generations per year in most places. Each generation consists of an egg stage, which hatches into ti larvae, which when fully grown, enter the *pupal* stage, during which metamorphosis occurs giving rise to the *adult* moth. These then mate and lay eggs so that the cycle begins over again. Thus, if moths are present in a locale, eggs and armyworms can be expected to appear there subsequently.

The presence of the moth in a locality is usually assessed by light trapping, wherein a bright light is used to lure the moths to a trap at night, during the periods when the moth is in flight. This technique has long been known and remains in wide use today. However, light lures indiscriminately bring many other moths, along with beetles and other insects, to the trap also; sorting is thus necessary. In practice, comparative light trapping is expensive and time-consuming, and expertise is required. A more convenient method of sampling local populations would use a simpler, cheap trap and a specific lure.

The compound (Z)-11-hexadecen-1-yl acetate (Z11-16:Ac) has been found in abdominal tip extracts and in effluvium from female moths of the common armyworm and has been confirmed as the primary sex pheromone component for *P. unipuncta* (see Hill and Roelofs "Environmental Entomology", Vol. 9, No. 4, p. 408–411, August 1980). McDonough et al, J. of Chem. Ecology, Vol. 6, No. 3, p. 565–572, 1980, also identified Z11-16:Ac, a hexadecen-1-ol (believed to be (Z)-11 isomer), and possible (Z)-9-hexadecen-1-yl acetate, in extracts of the female armyworm moths. In field tests, no combination of compounds was found to be more attractive than Z11-16:Ac alone. Farine et al confirmed the presence of Z11-16:OH in the natural extract and found (in addition to Z11-16:Ac) that hexadecanyl acetate and Z9-16:Ac were also present (see C.R. Acad. Sc. Paris, t. 292, Series III, p. 101–104, Jan. 5, 1981).

In early tests, we had found that Z11-16:Ac with 0.1–0.5% (Z)-11-hexadecenol produced a reasonably effective and specific lure for the male armyworm moths. The attraction was increased on adding trace amounts (e.g. 0.01%) of (Z)-9-tetradecen-1-yl acetate (Z9-14:Ac). (See W. Steck et al, "Environmental Entomology", Vol. 9, No. 5, p. 583–585, October 1980). In tests on *Polia atlantica* we had tried the ternary mixture Z11-16:Ac+Z11-16:OH+Z11-16:Ald in the weight ratios 200:1:1 and found it ineffective for this species (see Table 2 in this latter reference). Some or all of these latter three compounds are known to be present in attractants for other species but the ratios are vastly different and the previously described mixtures are substantially nonattractive to armyworm moths.

SUMMARY OF THE INVENTION

In further tests, we have found an unexpected benefit using a multicomponent attractant composition for moths of the armyworm *Pseudaletia unipuncta*, comprising:

(a) (Z)-11-hexadecenyl acetate,
(b) (Z)-11-hexadecenol,
(c) (Z)-11-hexadecenal, and
(d) (Z)-9-tetradecenyl acetate, in the approximate ranges of proportions by weight:
(a) 10000
(b) 1–200
(c) 1–50 and
(d) 0.1–2.

Even in the absence of (d) Z9-14: Ac, the attraction for armyworm moths is remarkably good with the ternary composition (a)+(b)+(c) in certain proportions. Thus the invention broadly comprises a method of attracting male armyworm moths *Pseudaletia unipuncta* during the flight period and in the expected locale of such moths, to specific loci or to disseminated attractant; comprising distributing by providing at each locus or by disseminating, an attractant composition comprising:

(a) (Z)-11-hexadecenyl acetate,
(b) (Z)-11-hexadecenol,
(c) (Z)-11-hexadecenal, optionally with
(d) (Z)-9-tetradecenyl acetate in the approximate proportions by weight
10,000:1–200:1–50:0—2
in an amount effective to attract such moths.

DESCRIPTION OF DRAWING

The single drawing is a bar chart of the relative attractancy of seven artificial attractants wit (a):(b) at 10000:20, taken as having an attractancy of 1. The result for A (no attractant) was obtained using an unbaited trap. This chart is a composite based on many field tests carried out from 1979–81.

DETAILED DESCRIPTION AND PREFERRED EMBODIMENTS

The presence of (d) Z9-14:Ac is optional though preferred. Trace amounts of (d) up to about 1 parts by weight per 10000 parts (a) Z11-16:Ac can be included. Best results have been obtained at the approximate relative proportions by weight (a):(b):(c):(d) of 10000:20:4:1. Even in the absence of (d), these proportions of (a), (b) and (c) give a relative attractancy over seven times as great as (a)+(b) at the same proportions, i.e. there is approximately an eightfold increase due to the aldehyde (c) Z11-16:Ald. With (d) added, the increase approaches elevenfold.

The rate of release of the attractant has been found to be important for optimum attractancy with a preferred range being about 0.2–4 micrograms per hour. Allowing for various climatic conditions, lower or higher rates gave poorer results. For dosage units of attractant on standard rubber septa, the range of about 0.3–1 mg gave best results and is preferred.

When these artificial attractants are used as lures in insect traps, male *P. unipuncta* moths, if present locally, are attracted strongly to the trap and can be monitored: other moths present in the trap locale are not attracted. A few males of *Helotropha reniformis* were found in some traps but only late in the season (September); the important interval for monitoring *P. unipuncta* is May through mid-July when *H. reinform is* is absent (North America).

The lure may be used to disrupt the mating of armyworm moths by dissemination over a substantial area, thus effecting population control of this pest. With other insects and their lures a direct relationship has been established between lure power/specificity and the ability to disrupt mating. The powerful and specific attractants described herein, thus should be very effective in disrupting mating.

The composition may, if desired, comprise a liquid or solid carrier or substrate. For example, suitable carriers or substrate include vegetable oils, refined mineral oils or fractions thereof, rubbers, plastics, silica, diatomaceous earth and cellulose powder. We have found a rubber carrier very suitable but other modes of dispensing are feasible.

The chemicals in the attractant are available commercially or can be synthesized and purified by published procedures.

The following examples are illustrative.

The chemical compounds used in the tests were synthesized in our laboratory by established routes and were 99% pure. Field trapping was carried out using cone traps as specified. Commercial traps used were Conor ]trademark] cone traps of Pherocon 1-CP [trademark] cone traps: otherwise, double-cone traps with entry port diameters cf 11–12 mm were used (as described by Steck et al, Environ. Entomol. 7, p. 449–455, 1978). This latter kind of trap eliminates chance captures almost entirely: unbaited control traps caught no moths. Red rubber septa of a type known to be effective in protecting aldehydes from oxidative destruction were used as dispensers. The release pattern is known to be a logarithmic decay, the half life depending on the volatility and stability of the compound applied. Specified amounts were applied in dilute (0.01) hexane solutions to the septum. Total doses were usually in the 100–1000 microgram range.

The sequence of test results leading up to the preset invention is given in the tables. Conclusions follow Tables 1–6. Additional test results are given in Table 7. Results are averaged and summarized in the bar chart. In the Tables, common letters follow means not different ($\sqrt{x+1}$ transformation, P=0.05) by Duncan's new multiple range test.

TABLE 1

Effect of Z11-16:OH and some other chemicals on lure attractancy for *Pseudaletia unipuncta* males. Pherocon 1-CP traps, 2 × Replicated. Saskatoon, Sask., 23 June–6 July, 1979

| Lure bait in traps | | | |
|---|---|---|---|
| Z11-16:Ac | Z11-16:OH | $3^{rd}$ Component | Moths trapped |
| 500 µg | 0 µg | none | 3 |
| 500 | 1 | none | 48 |
| 500 | 1 | Z9-16:Ac, 5 µg | 51 |
| 500 | 1 | Z9-14:Ac, 1 | 1 |
| 500 | 1 | A9-14:OH, 5 | 40 |

Conclusions:
1. 0.2% Z11-16:OH in lure enhanced trapping (48/3).
2. Neither Z9-16:Ac nor Z9-14:OH had significant effects.
3. 0.2% Z9-14:Ac suppressed trapping (1/48).

TABLE 2

Strength and specificity of *Pseudaletia unipuncta* lures containing various ratios of Z11-16:Ac/Z11-16:OH CONOR cone traps, 4 × Replicated. Saskatoon, Sask., 26 June–18 July, 1979

| Lure bait in traps | | Moths captured | | |
|---|---|---|---|---|
| Z11-16:Ac | Z11-16:OH | *P. unipuncta* | *S. trifolii* | other species |
| 500 µg | 0 µg | 22 c | 0 | 3 |
| 500 | 0.2 | 40 b | 0 | 0 |
| 500 | 1.0 | 83 a | 4 | 0 |
| 500 | 5.0 | 53 b | 82 | 8 |

Conclusions:
1. 500:1 gave best catch of *unipuncta*, at 90% specificity
2. Z11-16:OH above 0.2% decreased strength and especially specificity of lure.

TABLE 3

Captures of male *Pseudaletia unipuncta* moths in cone traps baited with lures containing Z11-16:Ac (500 µg) + Z11-16:OH (5 µg) + 3rd component, impregnated on red rubber septa dispersers. Single traps. Saskatoon, Sask., 20 June–26 July, 1979

| | *P. unipuncta* captures | | | | | | |
|---|---|---|---|---|---|---|---|
| 3rd Lure component | $1^{st}$ week | $2^{nd}$ week | $3^{rd}$ week | $4^{th}$ week | $5^{th}$ week | Total | *S. trifolli* |
| Z9-14:Ac, 5 µg | 0 | 0 | 0 | 0 | 0 | 0 | 4 |
| Z9-14:OH, 5 | 7 | 0 | 9 | 7 | 0 | 23 | 14 |
| Z9-16:Ac, 5 | 4 | 5 | 0 | 11 | 1 | 21 | 12 |
| Z11-16:Ald, 5 | 0 | 4 | 24 | 63 | 56 | 147 | 11 |

Conclusions:
1. Z11-16:Ald may be an important trace co-attractant; further tests must be performed next year (1980)

TABLE 4

Effect of various levels of (Z)—11-hexadecenal in the lure blend on captures of male *Pseudaletia unipuncta* moths by traps baited with synthetic acetate + alcohol, impregnated in red rubber septa for slow release. Test 4 × replicated. Saskatoon, Sask., 28 June–23 July, 1982

| Lure bait used in traps | Males trapped | |
|---|---|---|
| No bait | 0 | d |
| Z11-16 Ac (500 µg) + Z11-16:OH (2 µg) | 28 | bc |
| Z11-16 Ac (500 µg) + Z11-16:OH (2 µg) + Z11-16:Ald (0.05 µg) | 31 | b |
| Z11-16 Ac (500 µg) + Z11-16:OH (2 µg) + Z11-16:Ald (0.2 µg) | 61 | a |
| Z11-16 Ac (500 µg) + Z11-16:OH (2 µg) + Z11-16:Ald (0.5 µg) | 63 | a |
| Z11-16 Ac (500 µg) + Z11-16:OH (2 µg) + Z11-16:Ald (1.0 µg) | 20 | bc |
| Z11-16 Ac (500 µg) + Z11-16.OH (2 µg) + Z11-16:Ald (2.0 µg) | 3 | d |

Conclusions:
1. Ternary better than binary system; best Z11-16:Ald content range. (0.2–0.5 µg) corresponds to 0.04–0.1%
NOTE: The binary catch total involves one anomalously high trap so the figure of 28 may be somewhat higher than what might be reproducible.

TABLE 4A

Table 4 results including other species:
*Polia atlantica, Feltia ducens* and *Scotogramma trifolii*

| Lure bait used in traps | | | Males trapped | | | | |
|---|---|---|---|---|---|---|---|
| Z11-16:Ac | Z11-16:Oh | Z11-16:Ald | P. unipuncta | P. atlantica | F. ducens | S. trifolii | other |
| 0 μg | 0 μg | 0 μg | 0 | 0 | 0 | 0 | 0 |
| 500 | 0 | 0 | 2 | 0 | 5 | 0 | 1 |
| 500 | 2 | 0 | 28 | 0 | 5 | 4 | 2 |
| 500 | 2 | 0.05 | 31 | 0 | 4 | 3 | 0 |
| 500 | 2 | 0.2 | 61 | 0 | 4 | 1 | 0 |
| 500 | 2 | 0.5 | 63 | 16 | 0 | 3 | 2 |
| 500 | 2 | 1.0 | 20 | 34 | 2 | 4 | 0 |
| 500 | 2 | 2.0 | 3 | 101 | 0 | 1 | 0 |

Conclusion: 500 + 2 + 0.2 most specific lure (ca. 90%) as well as being high-potency lure.

TABLE 5

Effect of Z11-16:OH content on capture of males of *Helotropha reniformis* and *Scotogramma trifolii* by cone traps containing *P. unipuncta* lures. 3 × replicated. Saskatoon, Sask., 17-31 August 1982

| Lure bait used in traps | | | Moths captured* | |
|---|---|---|---|---|
| Z11-16:Ac | Z11-16:OH | Z11-16:Ald | H. reniformis | S. trifolii |
| 500 μg | 0 μg | 0.2 μg | 0 | 0 |
| 500 | 0.5 | 0.2 | 0 | 3 |
| 500 | 1.0 | 0.2 | 5 | 21 |
| 500 | 2.0 | 0.2 | 5 | 79 |

*The flight period of *P. unipuncta* was ended at this time.

Conclusions:
1. Both 0.5 and 1.0 μg Z11-16:OH (0.1 and 0.2% of lure) gave reduced captures of *S. trifolii* relative to 2.0 μg (0.4%) and therefore will give more specific *P. unipuncta* attraction. (Cf. Table 2)

TABLE 6

Captures of male *Pseudaletia unipuncta* moths in cone traps baited with synthetic chemical lures impregnated in red rubber septa for slow release. Test 4 × replicated at Saskatoon, Sask., 28 June-23 July 1982

| Lure bait used in traps | Males trapped | |
|---|---|---|
| No bait | 0 | c |
| Z11-16:Ac (500 μg) | 2 | c |
| Z11-16:Ac (500 μg) + Z11-16:OH (2 μg) | 28 | b |
| Z11-16:Ac (500 μg) + Z11-16:OH (2 μg) + Z11-16:Ald (0.2 μg) | 61 | a |
| Z11-16:Ac (500 μg) + Z11-16:OH (2 μg) + Z11-16:Ald (0.2 μg) + Z9-14:Ac (0.05) | 53 | ab |

Conclusions:
1. Ternary > Binary > Z11-16:Ac rank order of attractancy
2. Z11-16:Ac no better than unbaited traps
3. Addition of Z9-14:Ac did not increase captures, this is in contrast to 1979 tests. Z9-14:Ac is in any case not vital for full lure power.

TABLE 7

Cone trapping of *P. unipuncta* males using synthetic blends at Saskatoon, Sask.

| Lure Composition, μg | | | | Males captured[a] | |
|---|---|---|---|---|---|
| Z11-16:Ac | Z11-16:OH | Z11-16:Ald | Z9-14:Ac | P. unipuncta | Other species |
| Expt. A: 26 June-18 July 1979 (4 × replicated) | | | | | |
| 500 | 0 | 0 | 0 | 23 b | 0 |
| 500 | 0.2 | 0 | 0 | 36 ab | 0 |
| 500 | 1.0 | 0 | 0 | 88 a | 1 |
| 500 | 5.0 | 0 | 0 | 47 ab | 7 S. trifolii |
| Expt. B: 29 June-12 July 1979 (3 × replicated) | | | | | |
| 500 | 0.5 | 0 | 0 | 80 b | 3 |
| 500 | 0.5 | 0 | 0.005 | 97 ab | 2 |
| 500 | 0.5 | 0 | 0.05 | 131 a | 3 |
| 500 | 0.5 | 0 | 0.5 | 35 c | 7 |
| Expt. C: 3-15 June 1981 (4 × replicated) | | | | | |
| 500 | 1 | 0 | 0 | 5 cd | 1 |
| 500 | 1 | 0 | 0.005 | 16 bc | 2 |
| 500 | 1 | 0 | 0.02 | 5 cd | 2 |
| 500 | 1 | 0 | 0.05 | 9 cd | 2 |
| 500 | 1 | 0 | 0.5 | 1 d | 4 |
| 500 | 1 | 0.005 | 0.02 | 30 b | 1 |
| 500 | 1 | 0.05 | 0.02 | 29 b | 1 |
| 500 | 1 | 0.5 | 0.02 | 51 a | 1 |
| Expt. D: 16 June-6 July 1981 (4 × replicated) | | | | | |
| 500 | 1 | 0 | 0 | 7 bc | 3 |
| 500 | 1 | 0.005 | 0 | 16 bc | 1 |
| 500 | 1 | 0.05 | 0 | 25 b | 2 |
| 500 | 1 | 0.5 | 0 | 60 a | 0 |
| 500 | 1 | 5.0 | 0 | 0 c | 37 P. atlantica |
| 500 | 0 | 0 | 0 | 9 bc | 2 |

[a] Common letters follow means not different ($\sqrt{x+1}$ transformation, $P = 0.05$) by Duncan's new multiple range test.

The alcohol Z11-16:OH was essential for good trapping. Of the other trace components, the aldehyde was the more powerful synergist, giving captures about 8-fold better than the 2-component lure when present at 0.1% (50 ng) in a total lure of ca 500 μg. The acetate Z9-14:Ac increased lure power by only about 1.5-fold when present as 0.01% in the lure. At levels of 1% of either Z9-14:Ac or Z11-16:Ald, no *P. unipuncta* were taken, showing that the inhibition threshold for these compounds is below 1%. We experienced no particular difficulty in obtaining normal blend release lifetimes for nanogram amounts of Z11-16:Ald and Z9-14:Ac using rubber septa; the release of these trace compounds seemed to persist for at least two weeks. A dose of, for example, 50 ng may seem very small, but it represents about $10^{13}$ molecules and has the capability for normal prolonged release without rapid exhaustion of the material. In earlier experiments with lures for the noctuids *Polia atlantica* (Grote) and *Scotogramma farnhami* (Grote), both requiring trace amounts of olefinic aldehydes for attraction, we had similarly found that release of aldehydes continues for several weeks in the field. Thus there is no technical bar to using trace components in lures for field monitoring.

For *P. unipuncta*, a blend of Z11-16:Ac+Z11-16:Ald +Z9-14:Ac in ratios of 10000:20:5:1 offers a strong sex lure. Z9-14:Ac may be omitted from the blend without drammatically decreasing the lure power. On rubber septa, doses in the range 100–1000 μg resulted in best trapping. At least in North America, larger amounts of either Z11-16:OH or Z11-16:Ald in the blend are deleterious not only because captures of *P. unipuncta* are reduced, but also because other noctuid species begin to be attracted, as noted in the Tables.

We claim:

1. A multicomponent attractant composition for moths of the armyworm *Pseudaletia unipuncta*, comprising:
    (a) (Z)-11-hexadecenyl acetate
    (b) (Z)-11-hexadecenol
    (c) (Z)-11-hexadecenal and
    (d) (Z)-9-tetradecenyl acetate,
in the approximate ranges of proportions by weight:
    (a) 10,000
    (b) 1–200
    (c) 1–50 and
    (d) 0.1–2.

2. The attractant of claim 1 wherein (a) (b) and (c) are present in the approximate relative proportions 10,000:20:4.

3. The attractant of claim 2 including (d) in the approximate relative proportion of 1.

4. The attractant composition of claim 1 in dosage unit form adapted to have a rate of release of the order of 0.2–4 micrograms per hour.

5. The attractant composition of claim 4 in combination with a carrier, the composition being present in dosage units within the approximate range 0.3–1 mg.

6. The attractant-carrier dosage unit of claim 5 located in an insect trap.

7. A method of attracting male armyworm moth *Pseudaletia unipuncta* during the flight period and in the expected locale of such moths, to specific loci or to disseminated attractant; comprising distributing by providing at each locus or by disseminating, an attractant composition comprising:
    (a) (Z)-11-hexadecenyl acetate
    (b) (Z)-11-hexadecenol
    (c) (Z)-11-hexadecenal
optionally with
    (d) (Z)-9-tetradecenyl acetate,
in the approximate respective proportions by weight:
    10,000:1–200:1–50:0–2.
in an amount effective to attract such moths.

8. The method of claim 7 wherein (a), (b) and (c) are utilized in the approximate relative proportions: 10,000:20.4.

9. The method of claim 8 wherein the attractant also includes (d) in the approximate relative proportion of 1.

10. The method or claim 7 wherein the rate of release of the attractant from each locus is of the order of 0.2–4 micrograms per hour.

11. The method of claim 10 wherein the attractant is utilized in dosage units within the approximate range 0.3–1 mg.

* * * * *